United States Patent
Boda et al.

(10) Patent No.: US 9,055,873 B2
(45) Date of Patent: Jun. 16, 2015

(54) METHOD AND SYSTEM FOR MAINTAINING ISO CENTER CONSTANT IN AN ISO CENTRIC X-RAY IMAGING SYSTEM

(75) Inventors: Hiteshkumar T. Boda, Bangalore (IN); Gurudatt S. Kamat, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 671 days.

(21) Appl. No.: 13/332,287

(22) Filed: Dec. 20, 2011

(65) Prior Publication Data

US 2013/0156152 A1    Jun. 20, 2013

(30) Foreign Application Priority Data

Dec. 29, 2010    (IN) .......................... 4003/CHE/2010

(51) Int. Cl.
*A61B 6/00* (2006.01)
*A61B 6/03* (2006.01)
*A61N 5/10* (2006.01)
*A61B 6/04* (2006.01)

(52) U.S. Cl.
CPC ............... *A61B 6/03* (2013.01); *A61N 5/1069* (2013.01); *A61N 5/1049* (2013.01); *A61B 6/0492* (2013.01); *A61B 6/04* (2013.01); *A61B 6/0457* (2013.01); *A61B 6/4441* (2013.01); *A61B 6/469* (2013.01); *A61B 6/542* (2013.01); *A61B 6/547* (2013.01); *A61B 6/58* (2013.01)

(58) Field of Classification Search
CPC ...... A61B 6/04; A61B 6/0457; A61B 6/0492; A61B 6/08; A61B 6/547; A61N 5/1048; A61N 5/1049; A61N 5/1064; A61N 5/1069; A61N 5/107
See application file for complete search history.

(56) References Cited

U.S. PATENT DOCUMENTS

| | | | | |
|---|---|---|---|---|
| 4,481,657 | A | * | 11/1984 | Larsson ........................ 378/209 |
| 4,884,293 | A | * | 11/1989 | Koyama ........................ 378/197 |
| 6,315,446 | B1 | * | 11/2001 | Kidd et al. .................... 378/197 |
| 7,000,271 | B2 | | 2/2006 | Varadharajulu |
| 7,907,699 | B2 | * | 3/2011 | Long et al. ...................... 378/65 |
| 2002/0090058 | A1 | | 7/2002 | Yasuda et al. |
| 2004/0172757 | A1 | * | 9/2004 | Somasundaram ................ 5/601 |

(Continued)

FOREIGN PATENT DOCUMENTS

| | | |
|---|---|---|
| DE | 102008013613 A1 | 9/2009 |
| WO | 2007031945 A2 | 3/2007 |

OTHER PUBLICATIONS

Search Report and Written Opinion from corresponding EP Application No. 11194552.3 dated Mar. 19, 2012.

*Primary Examiner* — Thomas R Artman
(74) *Attorney, Agent, or Firm* — GE Global Patent Operation; Marc A. Vivenzio

(57) ABSTRACT

A method of maintaining a constant iso-center point, while dynamically changing an area of interest during an imaging procedure is provided. The method comprises: allowing a user to move from an initial area of interest to new area of interest by allowing permissible axes motions; dynamically calculating the iso-center point while moving from the initial area of interest to the new area of interest as a function of relative distance between the initial area of interest and the new area of interest and as a function of parameters indicating relative motion of permissible axes; identifying the new area of interest by using at least one permissible axis motion; and calculating the iso-center point at the new area of interest after locking all the permissible axes motions except table tilt axis movement.

14 Claims, 7 Drawing Sheets

(56) References Cited

U.S. PATENT DOCUMENTS

| | | |
|---|---|---|
| 2009/0036973 A1 | 2/2009 | Humphrey et al. |
| 2009/0238338 A1* | 9/2009 | Long et al. ............... 378/65 |
| 2010/0266186 A1 | 10/2010 | Hebrank et al. |
| 2011/0200171 A1* | 8/2011 | Beetel et al. ............ 378/65 |
| 2013/0156152 A1* | 6/2013 | Boda et al. ............... 378/20 |

* cited by examiner

METHOD AND SYSTEM FOR MAINTAINING ISO CENTER CONSTANT IN AN ISO CENTRIC X-RAY IMAGING SYSTEM

BACKGROUND OF THE INVENTION

1. Field of the Invention

This disclosure relates generally to X-ray imaging systems, more particularly to, method and system for maintaining iso-center constant while moving from one area of interest to another in an iso centric X-ray imaging system.

2. Description of the Prior Art

In an iso-centric X-ray imaging system, iso-center is defined to be a point in three dimensional space, where the center rays of the X-ray devices meet. The iso-center point is defined with reference to FIG. 1.

When a patient table is tilted, the iso-center point has to be kept constant. Currently, while tilting the patient table, all other axes motions are locked internally, so that the iso-center point is not lost and is kept constant. To keep the iso-center constant, during table tilt motion, the gantry is moved simultaneously. The iso-center is tracked continuously, and is kept a X-ray exposure as constant. This is called incidence keeping.

During an imaging procedure, it is required that the area of interest or focus has to be changed from one region or part of the body to another. During this time, the iso-center has to be shifted with reference to the new area of interest. For example, if the contrast agent flows quickly/slowly during a procedure, the area of interest may need to be shifted. Since there is no possibility of dynamically shifting iso-centers based on the new area of interest, it results in the following problems.

To focus on another area of interest, an operator/user/radiologist must come out of the current incidence keeping mode, position the gantry and the table in such a way that the new area of interest is in focus, and again start the incidence keeping. This requires excessive X-ray exposure to reach the intended area of interest and a considerable amount of time and effort.

Further, an operator/user/radiologist does not have instant access to the other axes of the system, to change the area of interest, as all the other axes are locked. This results in a lengthy workflow, wherein, there's a necessity to come out of the incidence keeping mode, manually position the table and/or the gantry to the required area of interest, and then go back to incidence keeping mode.

Thus, it would be beneficial to have a method and system for tracking the iso-center even while changing the area of interest.

BRIEF SUMMARY OF THE INVENTION

The above-mentioned shortcomings, disadvantages and problems are addressed herein which will be understood by reading and understanding the following specification.

According to one embodiment of the present invention, a method of maintaining a constant iso-center point, while dynamically changing an area of interest during an imaging procedure is provided. The method comprises: allowing a user to move from an initial area of interest to new area of interest by allowing permissible axes motions; dynamically calculating the iso-center point while moving from the initial area of interest to the new area of interest as a function of relative distance between the initial area of interest and the new area of interest and as a function of parameters indicating relative motion of permissible axes; identifying the new area of interest by using at least one permissible axis motion; and calculating the iso-center point at the new area of interest after locking all the permissible axes motions except table tilt axis movement.

According to another embodiment of the present invention, a method of maintaining a constant iso-center point and a constant X-ray exposure in an x-ray imaging system while moving from one area of interest to another area of interest, the imaging system comprising a movable patient table and a rotatable gantry, is provided. The method comprises: calculating an iso-center point with reference to an initial area of interest; unlocking at least one axis motion from the defined iso-center point corresponding to the initial area of interest; manually altering at least one axis motion along with a patient table tilt movement to locate a new area of interest; dynamically tracking the iso-center point at a given instance using the constant axis motion parameters along with relative motion of variable axes; stopping other axis motion except patient table tilt movement upon identifying the new area of interest; and calculating the iso-center point with reference to the new area of interest using all the axes motion parameters.

According to another embodiment of the present invention, an iso-center based imaging system is provided. The imaging system comprises: a movable patient table; a rotatable gantry; and a processor configured to control the movements of the gantry and the patient table. The processor comprises: a tracking module configured to dynamically calculate the iso-center point while moving from one area of interest to another, using the relative motion of all unlocked axes; and a fixing module configured to compute the iso-center point corresponding to the identified area of interest using all the axes information.

DETAILED DESCRIPTION OF THE INVENTION

Figure 1:
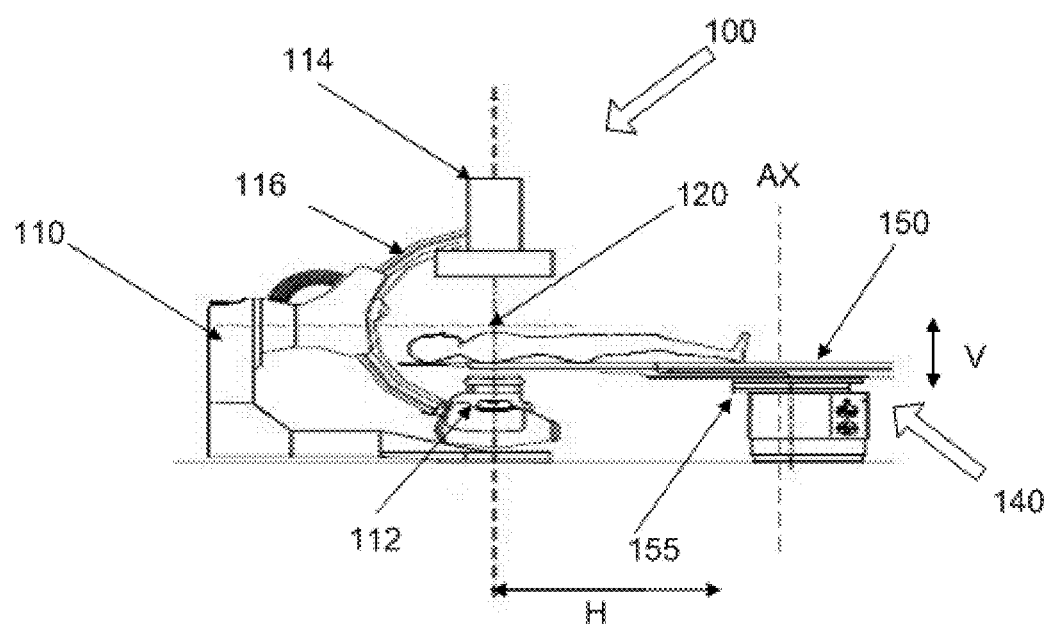
FIG. 1 illustrates the iso-center point in an X-ray imaging system as described in various embodiments of the invention.

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention. To the extent that the figures illustrate diagrams of the functional blocks of various embodiments, the functional blocks are not necessarily indicative of the division between hardware circuitry. Thus, for example, one or more of the functional blocks may be implemented in as single unit. It should be understood that the various embodiments are not limited to the arrangements and instrumentality shown in the drawings.

In various embodiments, an incidence keeping method for a change in areas of interest is disclosed. The iso-center is tracked dynamically while changing the area of interests and upon identifying the new area of interest the iso-center point is re-computed.

FIG. 1 illustrates the iso-center point in an X-ray imaging system as described in various embodiments of the invention. As shown, the imaging system 100 has a gantry 110 supporting by an arc-shaped arm 116 an X-ray generator 112 and an X-ray detector 114 facing the X-ray generator 112. The gantry 110 has an iso-center 120 in a space between the X-ray generator 112 and the X-ray detector 114. The iso-center 120 corresponds to a center of the arc of the arm 116. By moving the arm 116 along the arc by a feed mechanism incorporated, the X-ray generator 112 and the X-ray detector 114 rotate around the iso-center 120 while maintaining their facing relationship.

Figure 2:
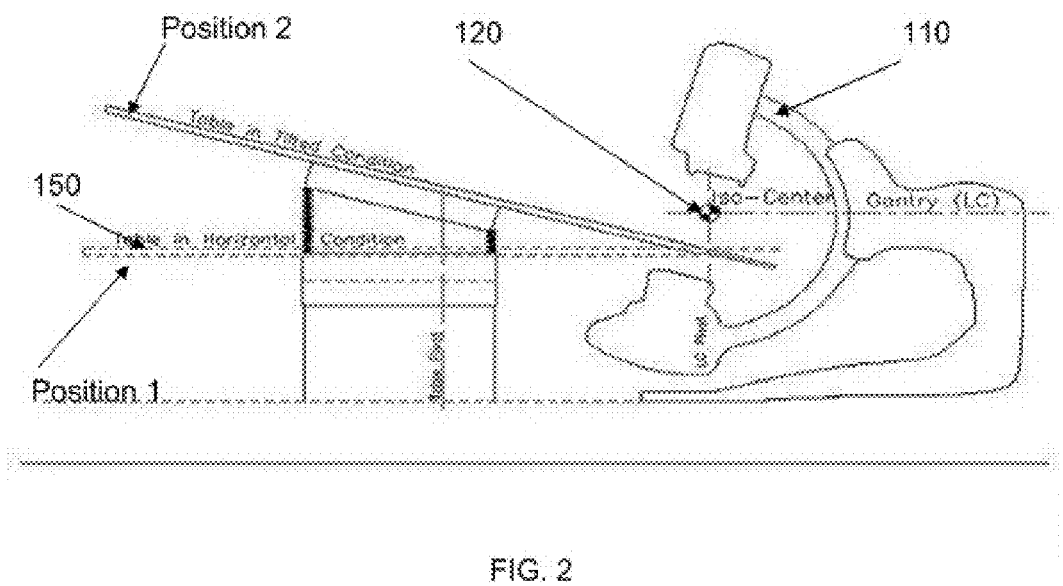
FIG. 2 illustrates incidence keeping in an X-ray imaging system as described in various embodiments of the invention.

The imaging system includes a patient table 140 carrying the patient. The patient table 140 has a table top 150, which is supported by a support base 155. In FIG. 2, a horizontal state of the table top 150 is shown. The support base 155 has an axis of rotation AX of the table top 150. The table top 150 is allowed to rotate around the axis of rotation AX in a horizontal plane. The position of the support base 155 is represented by the position of the axis of rotation AX. The support base 155 lies at a horizontal distance V from the iso-center 120 of the gantry 110 and the iso-center is at a height H from the support base 155. The support base 155 is the tilt hinge point, reference to which the patient table top 150 tilts or rotates.

The iso-center point 120 depends on the vertical distance V and the horizontal distance H from the support base 155 and the tilt angle. V is the vertical the distance from support base 155 to the iso-center point 120 and H is the horizontal distance from the support base 155 to the iso-center point 120. However the iso-center is kept constant while tilting the table top 150 by simultaneously rotating the gantry 110 rotation. This is called incidence keeping and is explained with reference to FIG. 2.

Though the figure is explained with reference to a C-arm, the method is applicable to any type of gantry system and, based on the structure of the gantry system, the iso-center point could be defined accordingly.

FIG. 2 illustrates incidence keeping in an X-ray imaging system as described in with reference to FIG. 1. Initially, the patient table top 150 is in the horizontal position as shown in position 1 and while the imaging proceeds, the table top 150 has to be titled to a position as shown in position 2. When the patient table top 150 is tilted from position 1 to position 2, the iso-center point 120 has to be kept constant. This is done by moving the gantry 110 simultaneously along with the tilt movement of the table top 150. Thus the simultaneous rotation of the gantry 110, and/or other axes motion of the patient table along with the tilt movement of the table top 150 will ensure that the iso-center point 120 is kept constant. This is called incidence keeping.

Figure 3:
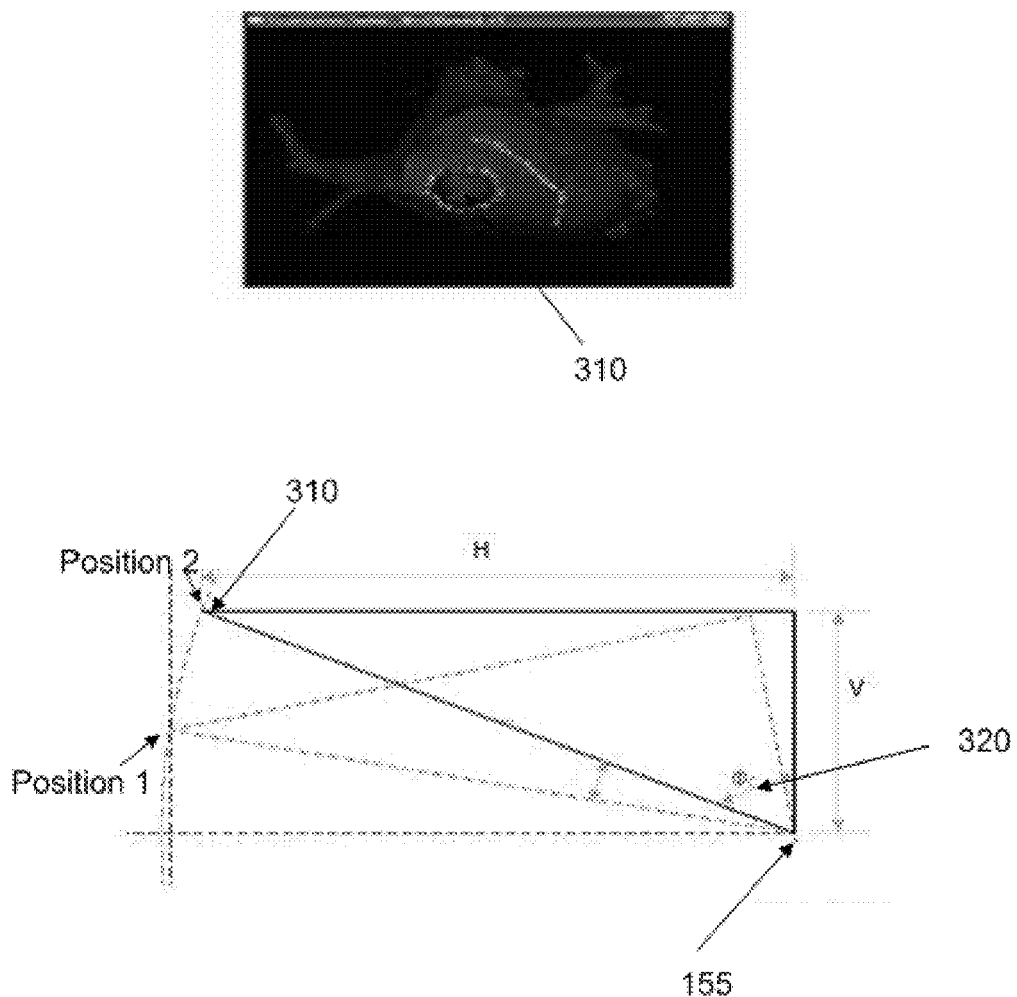
FIG. 3 illustrates method of keeping iso-center constant for an initial area of interest as described in an embodiment of the invention.

FIG. 3 illustrates a method of keeping the iso-center constant for an initial area of interest as described in an embodiment of the invention. Consider a scenario where a procedure is ongoing and the user is viewing a certain area/part of the body. The focus area or initial area of interest is marked as 310 and is at position 1 when the patient table top is in a horizontal position. When the patient table top is titled to a tilt angle φ 320, the area of interest 310 is also tilted as shown by position 2. The patient table top is tilted with reference to the tilt hinge point or the support base 155. To keep the area of interest 310 at the center of the image, the system would dynamically need to change the horizontal distance (H) and the vertical height (V) for a change in the tilt motion. Patient table axes motion i.e. longitudinal motion and lift motion, is represented as follows:

Movement of Longitudinal and Lift=$f(H,V,$Tilt angle$)$

To keep the iso-center constant, the gantry has to be moved simultaneously. The angulations are kept constant by dynamically changing Pivot and C-arc (gantry axis) for the same change in tilt motion. Gantry axes motion i.e Pivot and C-arc motion is represented as follows:

Movement of C,Pivot=$f($Tilt angle, constant CRA/CAU, Left Anterior Oblique (LAO)/Right Anterior Oblique (RAO)$)$.

The table and gantry axis motions are controlled for a change in tilt motion. Hence these axes are locked internally and not allowed to be controlled by the user.

The iso-center point is calculated using the patient table axes parameters including current longitudinal (H) and lift (V) position of the patient table and the table tilt angle and gantry axes parameters, including gantry tilt angle, pivot and C-arc position of the gantry. The iso-center point can be calculated by any existing formula, which includes the table axes motion parameters and gantry axes motion parameters.

Figure 4:
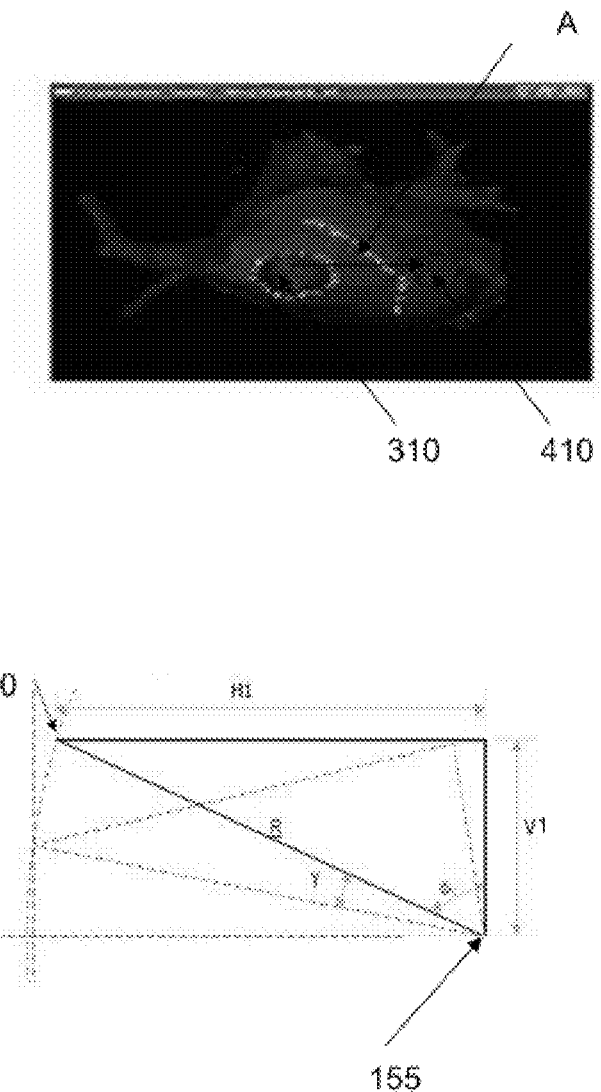
FIG. 4 illustrates method of keeping iso-center constant for a new area of interest as described in an embodiment of the invention.

FIG. 4 illustrates a method of keeping the iso-center constant for a change in the area of interest as described in an embodiment of the invention.

During the same procedure illustrated with reference to FIG. 3, the user now wishes to observe a new area of interest 410, which is at a distance A from initial area of interest 310.

In an embodiment of the invention, to view this point on the image, the user moves from an initial area of interest 310 to a new area of interest 410, while continuing the incidence keeping. As mentioned earlier during tilt movement of the patient the gantry motion and patient table axes motion cannot be controlled manually and are controlled automatically to keep the iso-center constant.

In an embodiment, the system allows the clinician to change the area of interest dynamically such that the user does not have to stop incidence keeping for viewing a different point of focus and can do so while incidence keeping is in process. This is achieved by keeping the iso-center point constant by calculating through a formula. This formula involves dynamic calculation based on the relative motion of all the axes as done by the operator/user/radiologist, in order to focus on the new area of interest. In this example, while incidence keeping is ongoing, the user would be able to move the longitudinal axis to point to the area of interest and still be able to keep the incidence. The iso-center point is computed dynamically as a function of relative distance between the areas of interest and as a function of parameters indicating relative motion of the axes used by the user, using the above mentioned formula. However it is to be noted that the incidence keeping can be continued even when the gantry axes moves or during any other axes motion of the patient table.

Hence by changing the longitudinal distance (H1), the vertical height (V1) and the delta between the initial and new area of interest, the new iso-center point is computed at the new area of interest.

Figure 5:
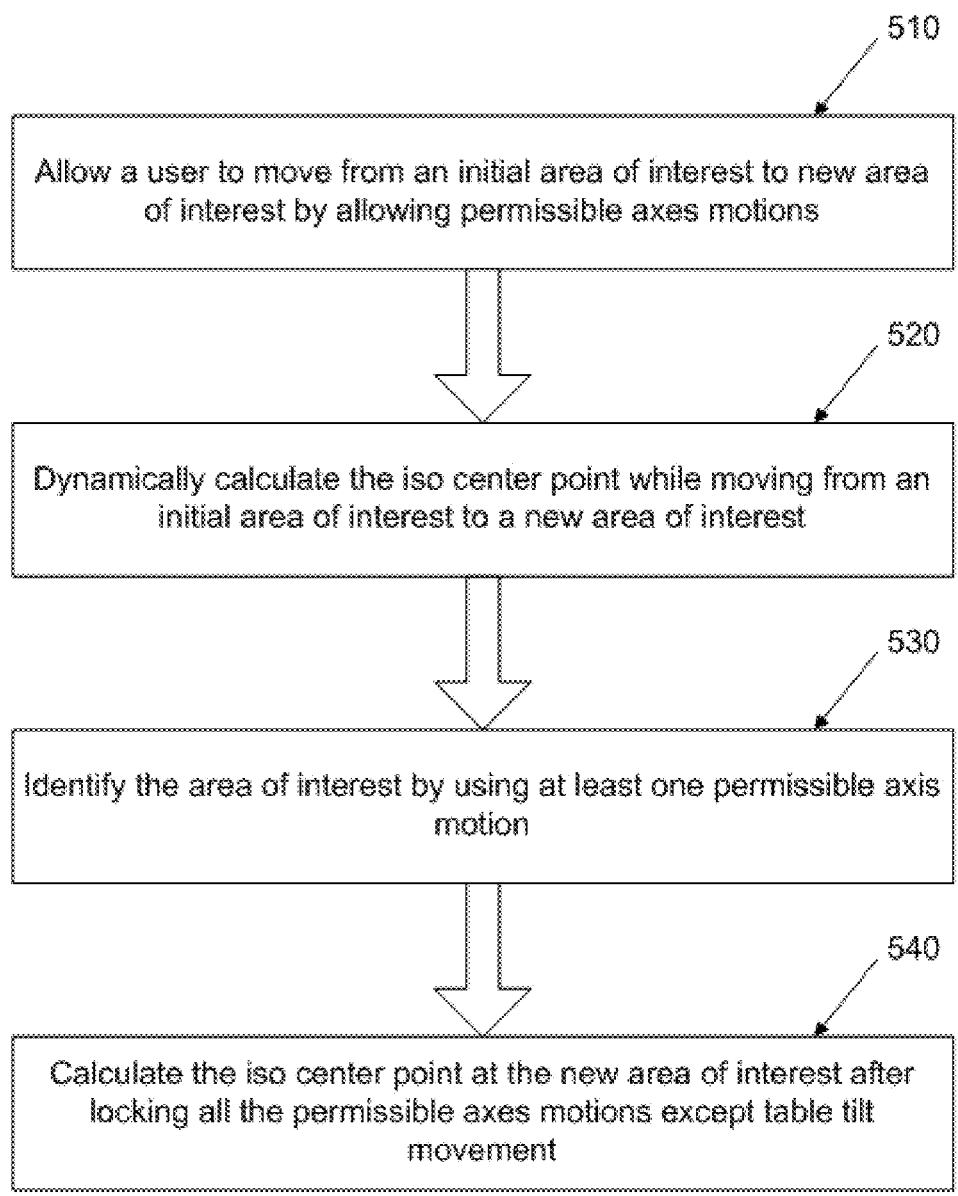
FIG. 5 is a flowchart illustrating method of keeping iso-center point constant as described in an embodiment of the invention.

FIG. 5 is a flowchart illustrating a method of keeping the iso-center point constant as described in an embodiment of the invention. At step 510, a user is allowed to dynamically move from one area of interest to another by allowing permissible axes motions. In an example, initially, except the table tilt movement all other axes motions will be locked for the user. At step 510, a user is allowed to control or move to the new area of interest using all permissible axes motion. The permissible axes motions could include table axes motion, gantry axes motion and the table tilt movement. For this, apart from the table tilt movement, some other axes motion such as table longitudinal or lift and gantry axes motion such as pivot or C-arc is allowed to be controlled by the user. At step 520, while moving the area of interest from the initial area of interest to the new area of interest, the system calculates the iso-center point dynamically. The iso-center point is calculated as a function of relative distance between the areas of interest and as a function of parameters indicating relative motion of permissible axes. At step 530, by using at least one of the permissible axes motion, the user identifies the new area of interest. The area of interest is identified by defining the new area of interest as a function of distance between the areas of interest. The area of interest is identified by moving the patient table and gantry in at least one of the permissible access motion until the defined area of interest is identified. At step 540, the iso-center point is calculated at the new area of interest after locking all axes motion except tilt motion of the table. The iso-center point at the new area of interest is calculated using patient table position and gantry position at the new area of interest and the relative distance between the areas of interest.

Figure 6:
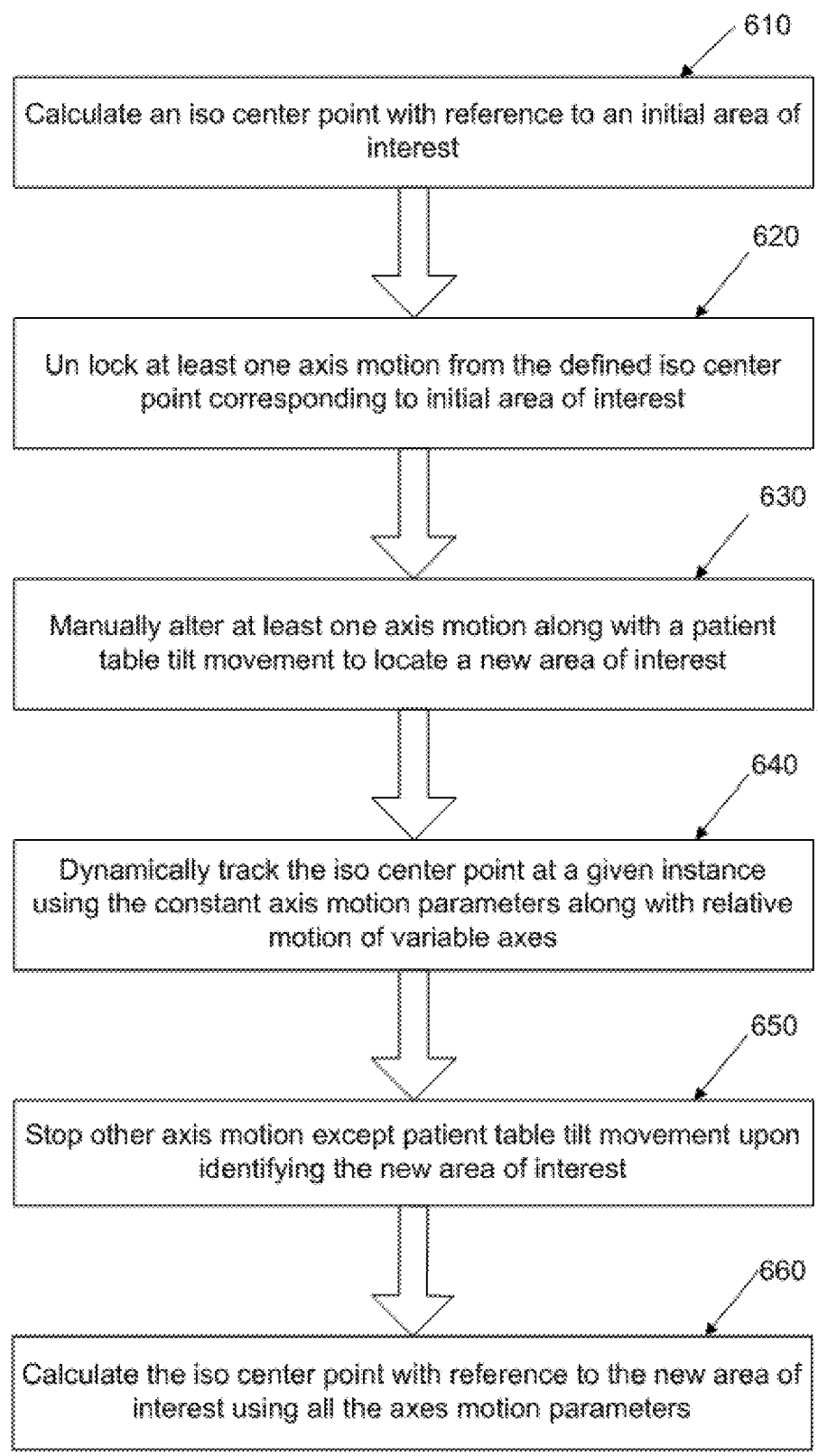
FIG. 6 is a detailed flowchart illustrating method of keeping iso-center point constant as described in an embodiment of the invention.

FIG. 6 is a flowchart illustrating a method of keeping the iso-center point constant as described in an embodiment of the invention. At step 610, an iso-center point is calculated with reference to the initial area of interest. While calculating the iso-center point, all axes motion, except table tilt movement, is locked. The term locked indicates that the other axes motions cannot be controlled by the user. The iso-center point is calculated using the patient table axes parameters including current longitudinal (H) and lift (V) position of the patient table and the table tilt angle and gantry axes parameters including gantry tilt angle, pivot and C-arc position of the gantry.

At step 620, at least one axes motion, apart from the tilt movement is un-locked. This allows the user to control or move the gantry or patient table in different directions. This will assist the user in identifying the new area of interest. At step 630, the user manually alters at least one axis motion along with a patient table tilt movement to locate a new area of interest.

At step 640, while moving the area of interest one to another, the iso-center point is tracked dynamically. The iso-center point is calculated using the relative axes motion parameters and the distance between the areas of interest at a given instance. The step includes tracking the iso-center point while moving the area of interest from initial area of interest to the new area of interest as a function of the relative distance between the initial area of interest and the new area of interest and as a function of all unlocked axes motion and distance from the area of interest.

At step 650, all other axes motion is stopped and locked, upon identifying the new area of interest. Only table tilt movement will be allowed to be controlled by the user, all other motions will be controlled internally. At step 660, the iso-center point is calculated at the new area of interest. At this point, all axes motion except table tilt movement will be locked. The iso-center at the new area of interest is calculated as a function of patient table axes parameters and gantry axes parameters at the new area of interest along with the distance between initial area of interest and new area of interest.

Figure 7:
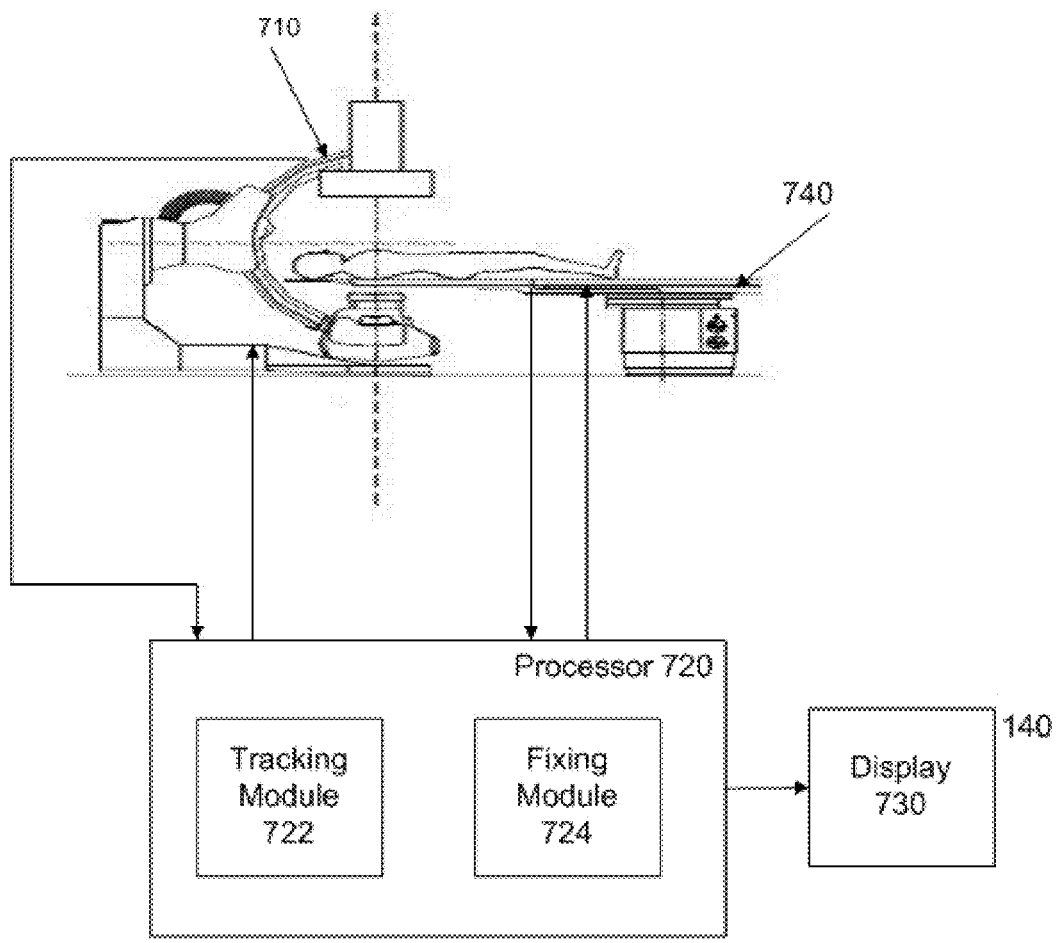
FIG. 7 is an X-ray imaging system having constant iso-center keeping feature as described in an embodiment of the invention

FIG. 7 is an X-ray imaging system having a constant iso-center keeping feature as described in an embodiment of the invention. The system is as described with reference to FIG. 1. The system includes a gantry 710 and a patient table 740. The system is further provided with a processor 720. The processor 720 is configured to track the iso-center point dynamically while the user changes the focus from one area of interest to another. The processor 720 includes a tracking module 722 and a fixing module 724. The tracking module 722 is configured to dynamically calculate the iso-center while the user moves from one area of interest to another. The iso-center point is calculated using the relative motion of all unlocked axes. The tracking module is configured calculate the iso-center point as function of all unlocked axes motion and distance from the area of interest.

The fixing module 724 is configured for computing the iso-center corresponding to the identified area of interest using all the axes information. The fixing module 724 is configured to calculate the iso-center point with reference to the initial and the new area of interest. The fixing module 724 is configured to calculate the iso-center point after locking all the axes motion except table tilt movement. The fixing module 724 is configured to calculate the iso-center point of the initial area of interest using patient table axes parameters including current longitudinal (H) and lift (V) position of the patient table position and the table tilt angle and gantry axes parameters including gantry tilt angle, pivot and C-arc position of the gantry. The fixing module 724 is configured to calculate the iso-center point with reference to the new area of interest as a function of patient table axes parameters and gantry axes parameters at the new area of interest along with the distance between the initial area of interest and the new area of interest.

The system further comprises a display 730 configured to display the area of interest while maintaining iso-center point constant. The display 730 may include the computer monitor or any other display associated with the processor 720.

Embodiments of the present invention can comprise software or firmware instructing a computer to perform certain actions. Some embodiments of the present invention comprise stand-alone workstation computers that include memory, a display, and a processor along with the imaging system. Whether a stand-alone workstation or an imaging system is used, software and/or firmware (hereinafter referred to generically as "software") can be used to instruct the computer to perform the inventive combination of actions described herein. Portions of the software may have specific functions, and these portions are herein referred to as "modules". However, in some embodiments, these modules may comprise one or more electronic hardware components or special-purpose hardware components that may be configured to perform the same purpose as the software module or to aid in the performance of the software module. Thus, a "module" may also refer to hardware or a combination of hardware and software performing a function.

The processor 720 may include dedicated hardware, software and/or firmware for performing information processing, or a combination of dedicated hardware and software, or software in combination with a general purpose processor, or a digital signal processor. Once the requirements for such software and/or hardware and/or dedicated hardware are gained from an understanding of the descriptions of embodiments of the invention contained herein, the choice of any particular implementation may be left to a hardware engineer and/or software engineer. However, any dedicated and/or special purpose hardware or special purpose processor is considered subsumed in the block labeled processor 720. The processor may include memory (not shown) for storing the image icons and the memory may include, for example, random access memory (RAM), flash memory, or read-only memory. For purposes of simplicity, devices that can read and/or write media on which computer programs are recorded are also included within the scope of the term "memory."

Thus various embodiments disclose a method and system for keeping the iso-center constant while changing the area of interest.

The advantages of the method and system allow the movement of the required axes according to the relative positions of all the other axes, without any outside interference, while still keeping the iso-center constant. It also ensures lesser doses of x-ray and contrast agents, resulting in a safer examination for patients.

As used herein, an element or step recited in the singular and proceeded with the word "a" or "an" should be understood as not excluding plural elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. Moreover, the terms "computer" and "processor" are used interchangeably herein to refer to either specialized hardware to perform digital signal processing, control, data manipulation, and/or calculations, or a general purpose computer that can be programmed to perform the same functions and/or adapted to interface with external digital signals.

Exemplary embodiments are described above in detail. The assemblies and methods are not limited to the specific embodiments described herein, but rather, components of each assembly and/or method may be utilized independently and separately from other components described herein. Further the steps involved in the workflow need not follow the sequence in which there are illustrated in figures and all the steps in the work flow need not be performed necessarily to complete the method.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

What is claimed is:

1. A method of maintaining a constant iso-center point while dynamically changing an area of interest during an imaging procedure, the method comprising:
    allowing a user to move from an initial area of interest to new area of interest by allowing permissible axes motions;
    dynamically calculating the iso-center point while moving from the initial area of interest to the new area of interest as a function of relative distance between the initial area of interest and the new area of interest and as a function of parameters indicating relative motion of permissible axes;
    identifying the new area of interest by using at least one permissible axis motion; and
    calculating the iso-center point at the new area of interest after locking all the permissible axes motions except table tilt axis movement.

2. The method as claimed in claim 1, wherein identifying the new area of interest comprises defining the new area of interest as a function of distance between the initial area of interest and the new area of interest.

3. The method as claimed in claim 1, wherein identifying the new area of interest comprises moving the patient table and gantry in at least one of the permissible axes motion until the defined area of interest is identified.

4. The method as claimed in claim 1, wherein calculating the iso-center point at the new area of interest comprises using patient table position and gantry position at the new area of interest and the relative distance between the initial area of interest and the new area of interest.

5. A method of maintaining a constant iso-center point and a constant X-ray exposure in an x-ray imaging system while moving from one area of interest to another area of interest, the imaging system comprising a movable patient table and a rotatable gantry, the method comprising:
    calculating an iso-center point with reference to an initial area of interest;
    unlocking at least one axis motion from the defined iso-center point corresponding to the initial area of interest;
    manually altering at least one axis motion along with a patient table tilt movement to locate a new area of interest;
    dynamically tracking the iso-center point at a given instance using the constant axis motion parameters along with relative motion of variable axes;
    stopping other axis motion except patient table tilt movement upon identifying the new area of interest; and
    calculating the iso-center point with reference to the new area of interest using all the axes motion parameters.

6. The method as claimed in claim 5, wherein calculating an iso-center point with reference to an initial area of interest comprises locking all axes motions except patient table tilt motion.

7. The method as claimed in claim 5, wherein calculating an iso-center point with reference to an initial area of interest comprises calculating the iso-center point_using patient table axes parameters including a current longitudinal position and a current lift position of the patient table and the table tilt angle and gantry axes parameters including gantry tilt angle, pivot and C-arc position of the gantry.

8. The method as claimed in claim 5, wherein dynamically tracking the iso-center point at a given instance comprises tracking the iso-center point while moving the area of interest from the initial area of interest to the new area of interest as a function of the relative distance between the initial area of interest and the new area of interest.

9. The method as claimed in claim 5, wherein dynamically tracking the iso-center point comprises calculating the iso-center point as function of all unlocked axes motion and distance from the area of interest.

10. The method as claimed in claim 5, wherein calculating the iso-center point with reference to the new area of interest comprises calculating the iso-center point as a function of patient table axes parameters and gantry axes parameters at the new area of interest along with the distance between the initial area of interest and the new area of interest.

11. An iso-center based imaging system comprising:
    a movable patient table;
    a rotatable gantry; and
    a processor configured to control the movements of the gantry and the patient table, the processor comprising:

a tracking module configured to dynamically calculate the iso-center point while moving from one area of interest to another, using the relative motion of all unlocked axes; and a fixing module configured to compute the iso-center point corresponding to the identified area of interest using all the axes information and calculate the iso-center point after locking all the axes motion except table tilt movement.

12. The system as claimed in claim 11, wherein the tracking module is configured to calculate the iso-center point as a function of all unlocked axes motion and distance from the identified area of interest.

13. The system as claimed in claim 11, wherein the fixing module is configured to calculate the iso-center point initially using patient table axes parameters including a current longitudinal position and a current lift position of the patient table position and the table tilt angle and gantry axes parameters including gantry tilt angle, pivot and C-arc position of the gantry.

14. The system as claimed in claim 11, wherein the fixing module is configured to calculate the iso-center point with reference to the new area of interest as a function of patient table axes parameters and gantry axes parameters at the new area of interest along with the distance between the initial area of interest and the new area of interest.

* * * * *